(12) United States Patent
Huentelman

(10) Patent No.: US 8,927,498 B2
(45) Date of Patent: Jan. 6, 2015

(54) COMPOSITIONS AND METHODS USEFUL IN ENHANCEMENT OF MEMORY

(75) Inventor: Matthew Huentelman, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 13/809,348

(22) PCT Filed: Jul. 11, 2011

(86) PCT No.: PCT/US2011/043610
§ 371 (c)(1),
(2), (4) Date: Feb. 22, 2013

(87) PCT Pub. No.: WO2012/006640
PCT Pub. Date: Jan. 12, 2012

(65) Prior Publication Data
US 2013/0196925 A1    Aug. 1, 2013

Related U.S. Application Data

(60) Provisional application No. 61/363,164, filed on Jul. 9, 2010.

(51) Int. Cl.
| | | |
|---|---|---|
| A61K 39/00 | (2006.01) | |
| A61K 39/385 | (2006.01) | |
| A01N 37/18 | (2006.01) | |
| C07K 14/47 | (2006.01) | |
| A61K 38/16 | (2006.01) | |
| A61K 38/17 | (2006.01) | |
| A61K 38/10 | (2006.01) | |
| A61K 45/06 | (2006.01) | |
| C07K 7/08 | (2006.01) | |

(52) U.S. Cl.
CPC .............. *C07K 14/47* (2013.01); *A61K 38/162* (2013.01); *A61K 38/1709* (2013.01); *A61K 38/10* (2013.01); *A61K 45/06* (2013.01); *C07K 7/08* (2013.01)
USPC ................... 514/17.7; 424/192.1; 424/193.1; 424/194.1

(58) Field of Classification Search
None
See application file for complete search history.

*Primary Examiner* — Olga N Chernyshev

(57) ABSTRACT

Compounds derived from a transduction complex that enhance memory in mammals and methods of enhancing memory using said compounds are disclosed.

15 Claims, 4 Drawing Sheets

COMPOSITIONS AND METHODS USEFUL IN ENHANCEMENT OF MEMORY

CROSS REFERENCE

This application is filed under 35 USC §371 from PCT Patent Application No. PCT/US2011/043610, which is related to and claims the priority benefit of U.S. provisional application 61/363,164, filed on Jul. 9, 2010, the teachings and content of which are incorporated by reference herein.

STATEMENT REGARDING FEDERALLY SPONSORED RESEARCH

This invention was made with government support under NS059873 awarded by the National Institutes of Health. The government has certain rights in this invention.

SEQUENCE LISTING

This application contains a sequence listing in computer readable format, the teachings and content of which are hereby incorporated by reference.

THE FIELD OF THE INVENTION

The present invention generally relates to compositions and methods for enhancing memory. In particular, the invention relates to a peptide based decoy that competes for phosphorylation with myristoylated alanine-rich C-kinase substrate (MARCKS).

BACKGROUND OF THE INVENTION

Peripheral administration of a rho-associated protein kinase (ROCK) inhibitor is capable of improving learning and working memory in an aged rat. Myristoylated alanine-rich C-kinase substrate (MARCKS) is one of the downstream targets of the RhoA/ROCK pathway and is known to participate in several key neuronal cell functions including neurite outgrowth and growth cone adhesion. SH-SY5Y cells stimulated with increasing doses of insulin-like growth factor (IGF-1) demonstrated a both significant and rapid decrease in phosphorylated MARCKS, and a significant increase in the number of neurite bearing cells. Additionally, memory formation occurs when neurons grow and make new connections. Therefore, inhibitors of MARCKS are needed as enhancers of memory. In addition, an association between the MARCKS protein and Alzheimer's disease (AD) was suggested. Phosphorylated MARCKS was detected in the β-Amyloid plaques of human hippocampal and parahippocampal brain tissue sections. Therefore, MARCKS' presence in the neuropathology of AD suggests a likely connection of MARCKS to AD.

BRIEF SUMMARY OF THE INVENTION

Briefly, therefore, one aspect of the present invention provides a biologically active peptide comprising a first sequence including SEQ ID NO: 2; and a second sequence selected from SEQ ID NO: 3, wherein the second sequence comprises a first serine residue, wherein the first serine residue is selected from the group comprising serine number 159 and serine number 163. In some forms, the first sequence of the biologically active peptide is SEQ ID NO: 2. In some forms, the biologically active peptide comprises a serine residue that is the MARCKS Ser159. In some forms, the biologically active peptide further comprises a second serine residue that is the MARCKS Ser159. In some forms, the biologically active peptide is represented by SEQ ID NO: 1.

Another aspect of the invention provides a method of enhancing memory in a mammal comprising administering an effective amount of a first pharmaceutical composition comprising SEQ ID NO: 1 to a subject. In some forms, the pharmaceutical composition further comprises a pharmaceutically acceptable carrier. In some forms, the subject is a mammal. In this provided method, the subject presents with memory loss. In some forms, the method further comprises the step of administering a second treatment modality to the subject, and the second treatment modality comprises a second pharmaceutical composition. In some forms of the method, administering the second pharmaceutical composition is concurrent with administering the first pharmaceutical composition. In some other forms, method provided comprises administering the second pharmaceutical composition prior to administering the first pharmaceutical composition. In yet another form of method, administering the second pharmaceutical composition is subsequent to administering the first pharmaceutical composition.

Other aspects and features of the invention are described more thoroughly below.

DETAILED DESCRIPTION OF THE INVENTION

Figure 1:
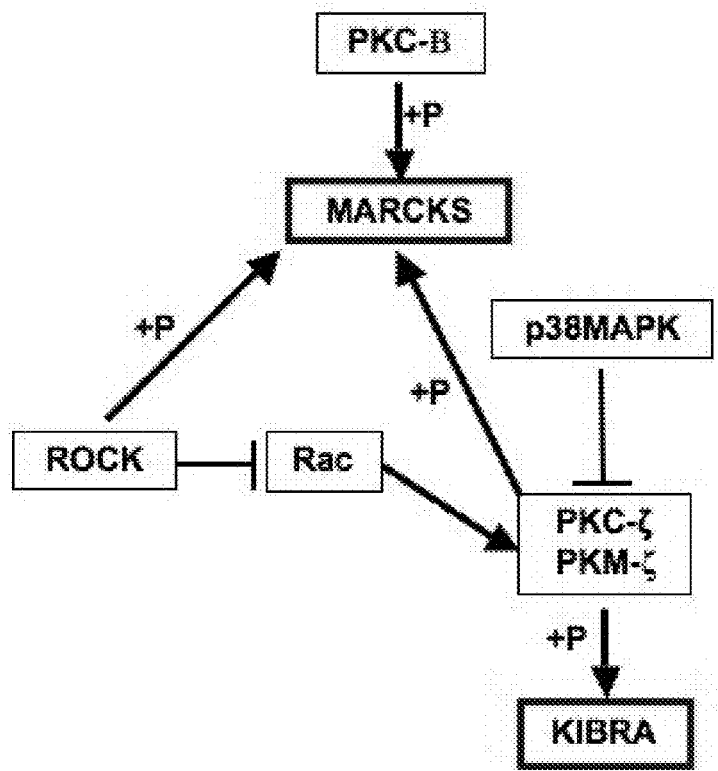
FIG. 1 depicts the MARCKS pathway.

Protein transduction domains (PTDs), also known as "cell penetrating peptides" (CPPs), possess the ability to translocate across biological membranes. PTDs are relatively short amino acid sequences that can be linked to a cargo moiety, allowing transport of the cargo moiety across a biological membrane, such as a cell membrane, an organelle membrane, and/or a nuclear membrane. Cargo moieties can include, for example, small molecules, macromolecules, lipids, liposomes, carbohydrates, proteins, or nucleic acids. In one embodiment, the cargo moiety may be a decoy. As used herein, a decoy is a peptide or a polynucleotide molecule that "competes" with consensus sequences in target genes or protein for binding of one or more molecules (e.g., transcription factors, other nucleic acid binding proteins, protein modification enzymes, chemical groups that modify amino acids). If delivered into the cell in sufficient concentrations, these "decoys" have the potential to attenuate the binding of a specific binding molecule and may thus attenuate the function or expression of a targeted protein or gene.

Naturally occurring PTDs have been derived from proteins which can efficiently pass through biological membranes. The best characterized of these PTDs are derived from the Drosophila homeoprotein antennapedia transcription protein (AntHD), the herpes simplex virus structural protein VP22, and the HIV-1 transcriptional activator TAT protein. Recent studies have also identified other PTDs, such as Mph-1 (U.S. Patent Application No. 20060148060); Sim-2 (Chrast et al., Genome Res. 7, 615-624 (1997)); and Pep-1 and Pep-2 (Morris et al., Nat. Biotech. 19:1173-1175 (2001)), SLPI-derived PTD (U.S. Patent Application No. 20110107443), arginine oligomers, among others. In addition, studies have isolated artificial PTDs and PTDs selected from random libraries (see, e.g., Joliot and Prochiantz, Nat. Cell Biol. 6(3):189-96 (2004)).

The invention provides a transduction complex which comprises (1) at least one PTD, and (2) at least one cargo moiety that is capable of being linked or fused to the PTD. A cargo moiety may comprise, for example, one or more polypeptides or fragments of a target protein; or one or more polynucleotides encoding part or all target protein; and optionally one or more small molecules, drugs, compounds, or labels. In one embodiment, the one or more polypeptides or fragments, or alternatively the one or more polynucleotides encoding the polypeptides thereof, comprise consensus serine sites for MARCKS phosphorylation. In one embodiment, the consensus serine sites are chosen from MARCKS serine 159 and serine 163. In other embodiments, the polypeptides or polynucleotide sequence of the cargo moiety of the transduction complex disclosed herein is selected for the ability of the polypeptides delivered (or polypeptides encoded by the polynucleotide sequence delivered by the PTD) to compete in vitro or in vivo the phosphorylation of MARCKS protein, and when delivered to the cell in sufficient concentrations, these "decoys" have the potential to attenuate the phosphorylation of MARCKS and may thus attenuate the ability of the protein to regulate the RhoA/ROCK pathway, restore the number of neurite bearing cells, and initiate the neurite outgrowth.

In one aspect, the transduction complex comprises at least one cargo moiety functioning as a decoy. A cargo moiety can be complexed to a PTD by any method known in the art and which is appropriate for a particular cargo moiety, providing that functionality of either the PTD or the cargo moiety is not destroyed. The skilled artisan will be able to choose the appropriate method to complex a cargo moiety with a PTD. Examples of such methods include, but are not limited to, chemical cross-linking with either a homobifunctional or heterobifunctional cross-linker, which may include a cleavage site; genetic fusion by, for example, linking a coding sequence for a PTD in-frame with a coding sequence for a polypeptide cargo moiety, wherein a cleavage site may be introduced between the two; and use of bridging molecules such as, for example, (a) streptavidin and biotin, (b) glutathione and glutathione-S-transferase, and (c) polyhistidine and an affinity chromatography reagent. These methods are well known in the art.

A skilled artisan will be able to determine if the respective parts of the transduction complex retain biological activity. The PTD retains biological activity if it can transport cargo across one or more biological membranes, e.g., a cell membrane and/or a nuclear membrane. Transport activity can be ascertained, for example, by adding the PTD cargo moiety complex to cells and assaying the cells to determine whether the cargo moiety was delivered across the biological membrane. One skilled in the art can determine if the cargo is located intracellularly or within the nucleus using methods well known in the art (e.g., immunohistochemical staining). The cargo moiety can be assayed for activity using a method acceptable for the type of cargo moiety. These assays are well known in the art and are described.

Figure 3:
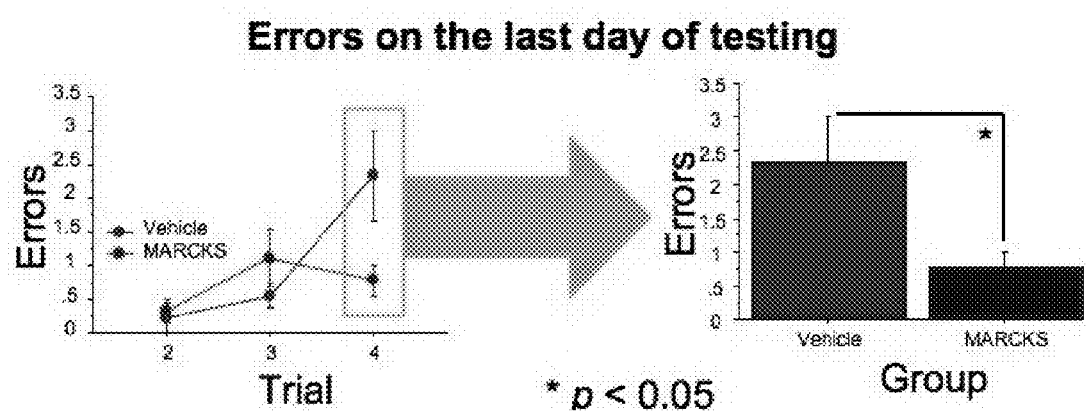
FIG. 3 depicts the results of the water-escape radial arm maze test.
Figure 4:
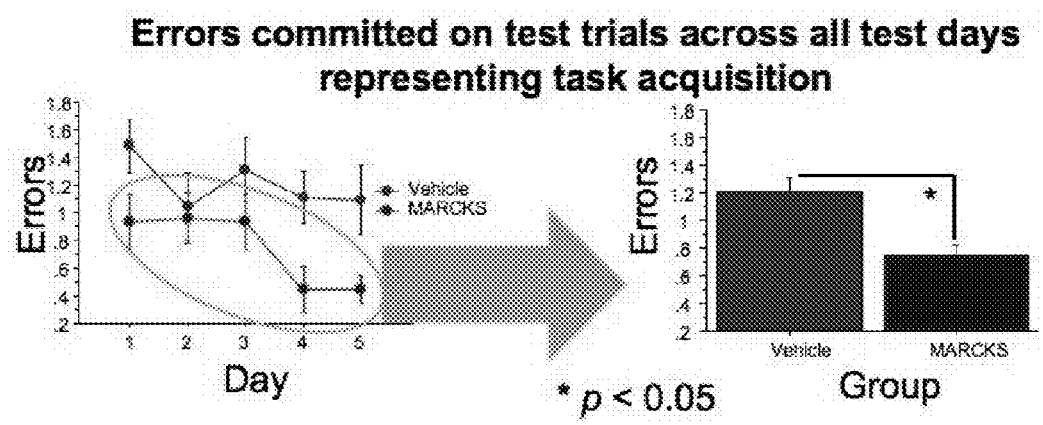
FIG. 4 depicts the results of the water-escape plus maze test.

In one embodiment of the present disclosed invention, the transduction complex comprises a fusion peptide including a TAT protein transduction domain and residues surrounding two known serine phosphorylation targets (Ser159 and Ser163) within MARCKS (SEQ ID NO: 3). The compound was administered to seventeen-month-old rats and behavioral spatial working memory of the rats was assessed by behavior testing. Behavioral assays can be used to determine whether or not an agent affects a particular phenotype exhibited by a non-human mammal. Such assays include, without limitation, the Morris water maze and the radial arm water maze, plus maze. For example, when employing the Morris water maze, a rat is trained to swim to a submerged platform. The rat can then be treated with an agent at a particular dose for a particular duration. Following treatment, the mean escape latency (i.e., time to find platform) is measured and compared to the mean escape latency of a control. When employing the radial arm water maze, a rat is trained to swim a path to a submerged platform during a first day of testing. On a second day of testing, the platform can be moved to a different location, and the rat can be trained to swim the new path to the submerged platform. In the invention disclosed herein, the rat can be treated with an agent at a particular dose for a particular duration at any time during the testing period. Following treatment, the ability of the rat to remember a newly-learned path is measured and compared to that of a control. As can be seen in the following Example 1, rats treated the biological active MARCKS peptide decoy, in accordance with the invention, has better performance in the radial arm water maze, whereas the controls were impaired as the memory loss was not alleviated such that more errors were made on the last day of testing (FIG. 3). In the water Plus Maze test, the variables measured include the percentage of time spent in the open and closed areas of the maze, the latency to leave the central platform, the total number of crossings between the various open and closed areas of the maze, and the number of crossings into the open areas of the maze divided by the total number of crossings. FIG. 4 showed significant difference between the rates treated with the MARCKS peptide decoy and the control group across all test days. Both behavioral tests showed that rats treated with the MARCKS peptide decoy have improved spatial working memory in comparison to the control group.

In one embodiment of the present disclosed invention, the transduction complex comprises a fusion peptide including a TAT protein transduction domain and residues surrounding two known serine phosphorylation targets (Ser159 and Ser163) within MARCKS (SEQ ID NO: 3). The compound was administered to seventeen-month-old rats and behavioral spatial working memory of the rats was assessed by behavior testing. Behavioral assays can be used to determine whether or not an agent affects a particular phenotype exhibited by a non-human mammal. Such assays include, without limitation, the Morris water maze and the radial arm water maze, plus maze. For example, when employing the Morris water maze, a rat is trained to swim to a submerged platform. The rat can then be treated with an agent at a particular dose for a particular duration. Following treatment, the mean escape latency (i.e., time to find platform) is measured and compared to the mean escape latency of a control. When employing the radial arm water maze, a rat is trained to swim a path to a submerged platform during a first day of testing. On a second day of testing, the platform can be moved to a different location, and the rat can be trained to swim the new path to the submerged platform. In the invention disclosed herein, the rat can be treated with an agent at a particular dose for a particular duration at any time during the testing period. Following treatment, the ability of the rat to remember a newly-learned path is measured and compared to that of a control. As can be seen in the following Example 1, rats treated the biological active MARCKS peptide decoy, in accordance with the invention, has better performance in the radial arm water maze, whereas the controls were impaired as the memory loss was not alleviated such that more errors were made on the last day of testing (FIG. 3). In the water Plus Maze test, the variables measured include the percentage of time spent in the open and closed areas of the maze, the latency to leave the central platform, the total number of crossings between the various open and closed areas of the maze, and the number of crossings into the open areas of the maze divided by the total number of crossings. FIG. 4 showed significant difference between the rates treated with the MARCKS peptide decoy and the control group across all test days. Both behavioral tests showed that rats treated with the MARCKS peptide decoy have improved spatial working memory in comparison to the control group.

Another aspect of the invention provides an isolated nucleic acid molecule encoding a polypeptide that comprises one or more PTDs and one or more cargo moieties linked to the one or more PTDs. Further, the isolated nucleic acid molecule may encode a linker polypeptide joining the PTD(s) and the cargo polypeptide(s). This linker polypeptide may optionally contain, for example, cleavage site(s) such that the PTD(s) can be cleaved from the cargo polypeptide(s) after delivery to the targeted intracellular compartment. The polypeptide cargo moiety can be complexed to either the amino terminus of the PTD or to the carboxy-terminus of the PTD. Alternatively or additionally, the polypeptide cargo moiety can be complexed to an internal residue of the PTD, e.g., by complexing to an internal side chain residue of the PTD directly or indirectly via a linking group, using methods available to the skilled worker.

The invention also provides a recombinant expression vector comprising an isolated nucleic acid molecule of the invention. The recombinant expression vector may be operably linked to an expression control sequence, which may, for example, comprise a promoter or enhancer that is specific to cells, tissues, or organs to which the vector is transduced. The vector preferably includes tag sequence(s), such as a series of Histidine, Hemaglutinin, Myc, or Maltose binding protein codons, for example, in order to facilitate purification of the vector. Further, a fusion partner such as lysine RNA polymerase may be introduced into the vector to increase solubility. One or more glycine and/or spacer amino acids may be incorporated to increase flexibility and stability of the fusion protein encoded by the vector. The vector may also comprise a cleavage site, which may be recognized by a protease specifically present in a certain intracellular compartment. This cleavage site may be used to separate the PTD and the cargo moiety, or to cleave another part of the fusion protein. In an alternative embodiment, the transduction complex may comprise one or more polynucleotides. Upon translocation into the cell, these polynucleotides may be introduced into the genetic material of the host and be translated into polypeptides comprising a PTD and one or more cargo moieties. A first polynucleotide of the transduction complex encodes a PTD that may be chosen from AntHD, VP22, TAT, SLPI, Mph-1; Sim-2, Pep-1, Pep-2, and arginine oligomers derived PTD.

In one embodiment, the polynucleotide encodes PTD derived from TAT, represented by SEQ ID NO:2. The additional one or more polynucleotides of the transduction complex may comprise one or more oligonucleotides encoding a peptide decoy. At least one oligonucleotide encodes a first polypeptide decoy cargo comprising one or more consensus serine sites that compete with target protein, MARCKS, for phosphorylation as disclosed herein. In another embodiment, an additional polynucleotide of the transduction complex encodes an optional second polypeptide cargo moiety comprising, e.g., agents that provide at least one therapeutic effect to the targeted cell, tissue, and/or subject. In another embodiment, an optional additional polynucleotide of the transduction complex encodes a polypeptide cargo moiety comprising, e.g., detectable enzymes or other reporter proteins, such as, for example, GFP, luciferase, and beta.-galactosidase.

To all above described sequences represented by its SEQ ID NO respectively, a sequence sharing about 60%, 65%, 70%, 75%, 80%, 85%, 90%, 95%, 99% or 100% identity to the described individual sequences is encompassed by the invention if polypeptides delivered (or polypeptides encoded by the polynucleotide sequence delivered by the PTD) is capable of binding to the complimentary sequences of the described individual sequences and is capable of competing in vitro or in vivo with the phosphorylation of MARCKS protein. "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

The invention also provides transformed cells and cell lines comprising the expression vector of the invention. Also provided are transgenic animals that produce one or more PTD fused peptide decoys of MARCKS of the invention. A transgenic plant or non-human animal comprising an isolated polynucleotide or polypeptide of the invention is included.

Another aspect of the invention provides a composition that comprises a transduction complex comprising one or more PTDs and one or more cargo moieties, or an isolated nucleic acid molecule encoding a polypeptide comprising one or more PTDs and one or more heterologous polypeptides, and a pharmaceutically acceptable carrier. The composition may also comprise a plurality of the host cells or cell lines of the invention. Compositions of the invention may further comprise one or more other components, such as therapeutic and/or diagnostic agents.

Delivery of the compositions and/or transduction complexes of the invention may take many forms. In one embodiment, a protein delivery method is disclosed. A polypeptide comprising one or more PTDs, optionally linked to one or more heterologous polypeptides, is purified from the genetically modified host cells or cell lines of the invention. The resulting polypeptide(s) are then optionally linked to other cargo moieties before delivery to a subject.

In another embodiment, a cell graft is used for delivery of fusion polypeptides. The graft comprises a plurality of genetically modified cells attached to a support, which is suitable for implantation into the subject. The support may be formed of a natural or synthetic material.

In yet another embodiment, an encapsulated cell expression system is used for delivery of fusion polypeptides. The encapsulated expression system comprises a plurality of genetically modified cells contained within a capsule, which is suitable for implantation into the subject. The capsule may be formed of a natural or synthetic material. The capsule containing the plurality of genetically modified cells may be implanted in, for example, the peritoneal cavity, the brain or ventricles in the brain, or into the specific disease site.

Pharmaceutical compositions comprising the transduction complex of this invention may be in a variety of forms, which may be selected according to the preferred modes of administration. These include, for example, solid, semi-solid and liquid dosage forms such as tablets, capsules, pills, powders, creams, liquid solutions or suspensions, syrups, suppositories, injectable and infusible solutions, aerosols and the like. The preferred form depends on the intended mode of administration and therapeutic application. Modes of administration may include, but are not limited to, oral, parenteral (including subcutaneous, intravenous, intramuscular, intra-articular, intra-synovial, cisternal, intrathecal, intrahepatic, intralesional and intracranial injection or infusion), topical, rectal, nasal, buccal, vaginal, by inhalation, or by an implanted reservoir, external pump or catheter.

The transduction complexes of this invention may, for example, be placed into sterile, isotonic formulations with or without cofactors which stimulate uptake or stability. The formulation is preferably liquid, or may be lyophilized powder. For example, an agent of the invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art. Such pharmaceutically acceptable carriers may include other medicinal agents, carriers, including genetic carriers, adjuvants, excipients, etc., such as human serum albumin or plasma preparations. The compositions are preferably in the form of a unit dose and will usually be administered one or more times a day.

The compositions comprising a compound of this invention will contain from about 0.1 to about 90% by weight of the active compound, and more generally from about 10% to about 30%. The compositions may contain common carriers and excipients, such as corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

For oral administration, the pharmaceutical compositions are in the form of, for example, a tablet, capsule, suspension or liquid. Solid formulations such as tablets and capsules are particularly useful. Sustained release or enterically coated preparations may also be devised. For pediatric and geriatric applications, suspensions, syrups and chewable tablets are especially suitable. The pharmaceutical composition is preferably made in the form of a dosage unit containing a therapeutically-effective amount of the active ingredient. Examples of such dosage units are tablets and capsules.

For therapeutic purposes, the tablets and capsules which can contain, in addition to the active ingredient, conventional carriers such as binding agents, for example, acacia gum, gelatin, methylcellulose, sodium carboxymethylcellulose, polyvinylpyrrolidone (Povidone), hydroxypropyl methylcellulose, sucrose, starch and ethylcellulose sorbitol, or tragacanth; fillers, for example, calcium phosphate, glycine, lactose, maize-starch, sorbitol, or sucrose; lubricants, for example, magnesium stearate, or other metallic stearates, stearic acid, polyethylene glycol, silicone fluid, talc, waxes, oils and silica, colloidal silica or talc; disintegrants, for example, potato starch, flavoring or coloring agents, or acceptable wetting agents.

Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Oral liquid preparations may comprise lipopeptide micelles or monomeric forms of the lipopeptide. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, a water soluble form of the transduction complex can be dissolved in any of the commonly used intravenous fluids and administered by infusion. Intravenous formulations may include carriers, excipients or stabilizers including, without limitation, calcium, human serum albumin, citrate, acetate, calcium chloride, carbonate, and other salts. Intravenous fluids include, without limitation, physiological saline or Ringer's solution. Polyamine and arginase modulators, optionally coupled to other carrier molecules, may also be placed in injectors, cannulae, catheters and lines.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. Lipopeptide micelles may be particularly desirable for parenteral administration. The compounds can be dissolved in polyethylene glycol, propylene glycol, ethanol, corn oil, benzyl alcohol, sodium chloride, and/or various buffers. For intramuscular preparations, a sterile formulation of a polyamine or arginase modulatory agent, or a suitable soluble salt form of the compound, for example a hydrochloride salt, can be dissolved and administered in a pharmaceutical diluent such as Water-for-Injection (WFI), physiological saline or 5% glucose.

Injectable depot forms may be made by forming microencapsulated matrices of the compound in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in microemulsions that are compatible with body tissues.

For topical use, the transduction complex of the present invention can also be prepared in suitable forms to be applied to the skin, or mucus membranes of the nose and throat, and can take the form of creams, ointments, liquid sprays or inhalants, lozenges, or throat paints. Such topical formulations further can include small molecules such as dimethylsulfoxide (DMSO) to facilitate surface penetration of the active ingredient. For topical preparations, a sterile formulation of a transduction complex or suitable salt forms thereof, may be administered in a cream, ointment, spray or other topical dressing. Topical preparations may also be in the form of bandages that have been impregnated with a therapeutic composition.

For application to the eyes, nose or ears, the transduction complex of the present invention can be presented in liquid or semi-liquid form optionally formulated in hydrophobic or hydrophilic bases as ointments, creams, lotions, paints or powders. For rectal or vaginal administration the compounds of the present invention can be administered in the form of suppositories admixed with conventional carriers such as cocoa butter, wax or other glyceride. For aerosol preparations, a sterile formulation of the peptide or lipopeptide or salt form of the compound may be used in inhalers, such as metered dose inhalers, and nebulizers.

Alternatively, the transduction complex of the present invention can be in powder form for reconstitution in the appropriate pharmaceutically acceptable carrier at the time of delivery. In one embodiment, the unit dosage form of the compound can be a solution of the compound or a salt thereof, in a suitable diluent in sterile, hermetically sealed ampules. The concentration of the compound in the unit dosage may vary, e.g. from about 1 percent to about 50 percent, depending on the compound used and its solubility and the dose desired by the physician. If the compositions contain dosage units, each dosage unit preferably contains from 0.1 to 10:mol/kg/hour of the active material. For adult human treatment, the dosage employed preferably ranges from 0.1 to 3.0:mol/kg/hour depending on the route and frequency of administration.

For subcutaneous administration, more preferred doses are 0.15-1.5:mol/kg/hour. Doses are administered for at least 24 hours, preferably 48 hours, more preferably 3 days, more preferably 1 week, more preferably 2 weeks, more preferably 3 weeks, 1 month, 2 months or longer. Doses may be administered for periods of up to 3 months, 6 months or 12 months or longer.

The pharmaceutical compositions of this invention may also be administered using microspheres, liposomes, other microparticulate delivery systems or controlled or sustained release formulations placed in, near, or otherwise in communication with affected tissues, the bloodstream, the cerebrospinal fluid, or other locations, including muscle, which enable the targeting of the agent to an affected location in the nervous system. The compositions of the invention can be delivered using controlled (e.g., capsules) or sustained release delivery systems (e.g., bioerodable matrices).

Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and gamma ethyl-L-glutamate (Sidman et al., Biopolymers 22:547-56 (1985)); poly(2-hydroxyethylmethacrylate) or ethylene vinyl acetate (Langer et al., J. Biomed. Mater. Res. 15:167-277 (1981); Langer, Chem. Tech. 12:98-105 (1982)).

Liposomes containing transduction complexes can be prepared by well-known methods (see, e.g. DE 3,218,121; Epstein et al., Proc. Natl. Acad. Sci. U.S.A. 82:3688-92 (1985); Hwang et al., Proc. Natl. Acad. Sci. U.S.A. 77:4030-34 (1980); U.S. Pat. Nos. 4,485,045 and 4,544,545). Ordinarily the liposomes are of the small (about 200-800 Angstroms) unilamellar type in which the lipid content is greater than about 30 mol. % cholesterol. The proportion of cholesterol is selected to control the optimal rate of agent release.

The transduction complexes of this invention may also be attached to liposomes, which may optionally contain other agents to aid in targeting or administration of the compositions to the desired treatment site. Attachment of such agents to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., J. Cell. Biochem. Abst. Suppl. 16E 77 (1992)).

Dosages and desired concentrations disclosed herein in pharmaceutical compositions of the present disclosure may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

The addition of a therapeutically effective amount of the disclosed transduction complexes encompasses any method of dosing of a compound. Dosing of the disclosed transduction complexes may include single or multiple administrations of any of a number of pharmaceutical compositions that include the disclosed transduction complexes as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

Pharmaceutical compositions that include the disclosed compound may be administered prior to, concurrently with, or after administration of a second pharmaceutical composition that may or may not include the compound. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

Yet another aspect of the invention provides kits comprising the transduction complex comprising one or more PTDs and one or more cargo moieties. At lease one of the cargo moieties is capable of competing with MARCKS for phosphorylation. Optional additional cargo moieties can be agents that provide at least one therapeutic effect to the targeted cell, tissue, and/or subject, or detectable enzymes or other reporter proteins, such as, for example, GFP, luciferase, and beta-galactosidase. The transduction complex of this invention can be supplied in single or divided aliquots, in single or divided containers. Written instructions can be included for using the complex. The instructions can be on the label or container. The instructions may simply refer a reader to another location such as a website or other information source.

The invention thus provides the art with reagents, methods, and uses for a peptide based decoy to attenuate the phosphorylation of MARCKS and may thus restore the number of neurite bearing cells, and initiate the neurite outgrowth. Pharmaceutical compositions including the disclosed transduction complex may be used in methods of treating memory loss or enhancing memory. Such methods involve the administration of an effective amount of a pharmaceutical composition that includes the disclosed compound and/or pharmaceutically acceptable derivatives thereof to a mammal.

In order to further define the invention, the following terms and definitions, unless otherwise indicated, shall be understood to have the following meanings:

The term "polypeptide" encompasses native or artificial proteins, protein fragments, and polypeptide analogs of a protein sequence. As used herein, the twenty conventional amino acids and their abbreviations follow conventional usage. See Immunology—A Synthesis (2.sup.nd Edition, E. S. Golub and D. R. Gren, Eds., Sinauer Associates, Sunderland, Mass. (1991)), incorporated herein by reference. When the amino acids are alpha-amino acids, either the L-optical isomer or the D-optical isomer can be used. A polypeptide encompasses an amino acid sequence and includes modified sequences such as glycoproteins, D-amino acid modified polypeptides, and the like. In addition, use of amino acid analogs is contemplated. Examples of amino acid analogs include, but are not limited to, ethyl esters, methyl esters, naphthylamides, and 7-amido-4-methyl coumarin. A polypeptide may be monomeric or polymeric. In certain embodiments, a polypeptide, whether monomeric or polymeric, comprises at least five, six, seven, eight or more amino acids.

In some embodiments, retro-inverso peptides are used. "Retro-inverso" means an amino-carboxy inversion as well as enantiomeric change in one or more amino acids (i.e., levantory (L) to dextrorotary (D)). A polypeptide of the disclosure encompasses, for example, amino-carboxy inversions of the amino acid sequence, amino-carboxy inversions containing one or more D-amino acids, and non-inverted sequence containing one or more D-amino acids. Retro-inverso peptidomimetics that are stable and retain bioactivity can be prepared as described by Brugidou et al. (Biochem. Biophys. Res. Comm. 214(2): 685-693 (1995)) and Chorev et al. (Trends Biotechnol. 13(10): 438-445 (1995)).

The term "isolated protein" or "isolated polypeptide" refers to a protein or polypeptide that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% w/w of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification and quantification.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long. The term "functional fragment" refers to fragments of a polypeptide that retain an activity of the polypeptide. For example, a functional fragment of a PTD comprises a fragment which retains transduction activity.

Polypeptides and fragments can have the same or substantially the same amino acid sequence as the naturally occurring protein. "Substantially identical" means that an amino acid sequence is largely, but not entirely, the same, but retains a functional activity of the sequence to which it is related. An example of a functional activity is transduction activity.

In general two amino acid sequences are "substantially identical" if they are at least about 85%, preferably at least about 90%, and more preferably at least about 95%, 96%, 97%, 98% or 99% or more identical, or if sequence variations consist of conservative amino acid substitutions. Conservative substitutions are defined as the exchange of one amino acid for another having similar properties. Examples of conservative substitutions include, but are not limited to 1) glycine and alanine; 2) valine, isoleucine, and leucine; 3) aspartic acid and glutamic acid; 4) lysine and arginine; 5) asparagine and glutamine; and 6) serine and threonine. A computer program, such as the BLAST program (Altschul et al., 1990) can be used to compare sequence identity.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), incorporated herein by reference.

The term "polynucleotide" refers to a polymeric form of nucleotides of at least 10 bases in length, either ribonucleotides or deoxynucleotides or a modified form of either type of nucleotide. The term includes single and double stranded forms. A reference to a nucleotide sequence encompasses its complement unless otherwise specified. Thus, a reference to a nucleic acid having a particular sequence should be understood to encompass its complementary strand, with its complementary sequence.

The term "isolated polynucleotide" refers to a polynucleotide of genomic, cDNA, or synthetic origin or some combination thereof, which by virtue of its origin: (1) is not associated with all or a portion of polynucleotides with which the "isolated polynucleotide" is found in nature, (2) is operably linked to a polynucleotide to which it is not linked in nature, or (3) does not occur in nature as part of a larger sequence.

"Operably linked" sequences are sequences that can be expressed together from the same expression control sequences, and/or used together to express a product of interest. Operably linked sequences include both expression control sequences that are contiguous with the gene of interest and expression control sequences that act in trans or at a distance to control the gene of interest. A nucleic acid encoding a SLPI-derived PTD may be operably linked to a nucleic acid encoding a cargo moiety in such a way that a fusion between the PTD and cargo moiety results upon expression in a host cell.

The term "expression control sequence" as used herein means polynucleotide sequences that are necessary to effect the expression and processing of coding sequences to which they are ligated or otherwise operably attached. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector," as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As used herein, the terms "label" or "labeled" refers to incorporation of another molecule in a polypeptide of the invention. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, .sup.111In, .sup.125I, .sup.131 I), fluorescent labels (e.g., FITC, rhodamine, lanthanide phosphors), enzymatic labels (e.g., horseradish peroxidase, .beta.-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "PTD" refers to a protein transduction domain, which is a Polypeptide sequence that is able to translocate across one or more biological membranes. PTD that can be used in the present invention is able to translocate into at least 50%, 60%, 70%, 80%, 90% or preferably 95%, 96%, 97%, 98%, 99% or 100% of cell types to which it is applied. Further, PTD that can be used in the present invention is able to translocate into at least 50%, 60%, 70%, 80%, 90% or preferably 95%, 96%, 97%, 98%, 99% or 100% of a population of cells to which it is applied.

As used herein, the phrase "therapeutically-effective amount" means an amount of a substance comprising a transduction complex of the invention such that the subject exhibits a therapeutic effect after being treated under the selected administration regime (e.g., the selected dosage levels and times of treatment).

The term "treating" is defined as administering, to a subject, a therapeutically-effective amount of a compound of the invention, to prevent the occurrence of symptoms, to control or eliminate symptoms, or to palliate symptoms associated with a condition, disease, or disorder associated with neuronal death or lack of neuronal growth.

The term "subject," as described herein, is defined as a mammal or a cell in culture. In a preferred embodiment, a subject is a human or other animal patient in need of treatment.

The term "patient" includes human and veterinary subjects.

In order that this invention be more fully understood, the following exampled are set forth. These examples are for the purpose of illustration only and are not to be construed as limiting the scope of the invention in any way.

EXAMPLES

The following specific examples are intended to illustrate the disclosure and should not be construed as limiting the scope of the claims.

Example 1

Spatial Working Memory Assessment Upon MARCKS Peptide Decoy Treatment

Figure 2:
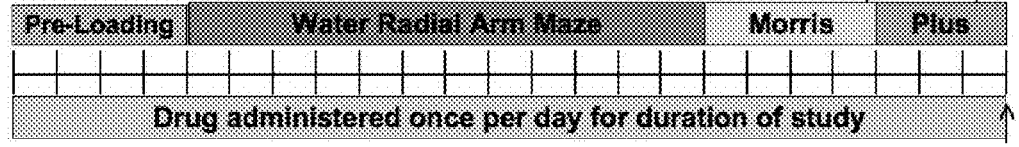
FIG. 2 depicts the study design.

A peptide-based MARCKS phosphorylation decoy was developed and tested for effects on memory performance. The aged rat model of cognitive decline was employed. The compound comprises a fusion peptide including a TAT protein transduction domain and residues surrounding two known serine phosphorylation targets (Ser159 and Ser163) within MARCKS (SEQ ID NO: 3). The compound was administered to seventeen-month-old Fischer-344 male rats at a dose of 1 mg/kg/day (n=9). Control animals of the same age were treated with the vehicle (saline, n=9). Dosing was initiated three days prior to behavior testing and continued throughout the experiment until sacrifice. Spatial working memory was assessed using water-escape versions of the plus maze and the radial-arm maze, and the experiment design was illustrated in FIG. 2.

Referring now to FIG. 3, animals treated with SEQ ID NO: 1 were better able to process multiple items of information as compared to animals receiving vehicle alone. This result indicates that SEQ ID NO: 1 enhances working memory systems.

Referring now to FIG. 4, animals treated with SEQ ID NO: 1 acquired the plus maze task at a faster rate when compared to animals receiving vehicle alone. This suggests that SEQ ID NO: 1 enhances working memory systems.

Behavioral results demonstrated that treatment with SEQ ID NO: 1 enhanced working memory performance in both mazes (plus maze: $t(16)=4.91$; $p<0.05$ and radial arm maze: $t(16)=4.38$; $p<0.05$). The partial blockade of MARCKS phosphorylation by way of a decoy peptide represented by SEQ ID NO: 1 can enhance working memory and support a role for MARCKS in the process of working memory.

Example 2

Transcriptome Examination Using RNA-Seq Upon MARCKS Peptide Decoy Treatment

Following sacrifice, the left hippocampus was utilized for genome-wide expression profiling. In addition, significant gene expression changes were noted for transcripts involved with learning, memory, neuronal plasticity and neuronal migration. These included Adcyap1 with fold change (FC) of 1.5, and p=0.029, Tiam1 with FC of −1.5 and p=0.028, and Filip1 with FC of −1.75 and p=0.032 (Table 1). The RT-PCR validation of the fold change of FILIP1 and Tiam1 is shown in Table 2 and Table 3, respectively.

TABLE 1

Hippocampal expression of candidate genes in rats treated with SEQ ID NO. 1 vs. vehicle treated rats as determined by the Illumina RatRef-12 expression BeadChip.

| Candidate Genes | T-Test | | Mann-Whitney | |
| --- | --- | --- | --- | --- |
| | Diff. PVal | Fold Change | Diff. PVal | Fold Change |
| Adcyap1 | 0.043 | 1.554 | — | — |
| Filip1 | 0.046 | −1.747 | 0.004 | −1.747 |
| Gna1 | — | — | 0.031 | −1.534 |
| LOC501145 | 0.038 | 1.566 | — | — |
| Perp_predicted | 0.036 | −1.647 | — | — |
| Ptpro | — | — | 0.040 | −1.708 |
| Tiam1 | 0.047 | −1.499 | 0.031 | −1.510 |
| Tp53i11_predicted | 0.032 | −1.554 | 0.004 | −1.581 |

TABLE 2

RT-PCR validation of FILIP1 (normalized to GAPDH)

| | Average | StDev | P-Value |
|---|---|---|---|
| SEQ ID NO: 1 (n = 9) | 1.20 | 0.061 | 0.023 |
| Vehicle (n = 9) | 1.28 | 0.069 | |

TABLE 3

RT-PCR Validation of Tiam1 normalized to GADPH

| | Average | StDev | P-Value |
|---|---|---|---|
| MARCKS (n = 9) | 0.89 | 0.088 | 0.011 |
| Vehicle (n = 9) | 1.02 | 0.102 | |

Table 4 disclosed herein provides the major pathways in mitochondria altered in the MARCKS peptide decoy treated animals. The fold changes indicated in the table are significant. Mitochondrial NADH dehydrogenase is a key enzyme in the oxidative phosphorylation pathway in the mitochondria. Mitochondrially encoded cytochrome c oxidase I (MT-CO1), also known as cytochrome c oxidase I (COX1), is a protein that is found in mitochondria. Cytochrome c oxidase is the component of the respiratory chain that catalyzes the reduction of oxygen to water. MT-CO1 is associated with aging. Mutations in the human MT-CO1 gene have been associated with several diseases, including neurodegenerative diseases, such as late-onset Alzheimer disease. Cytochrome b (mt-cyb) is a component of the ubiquinol-cytochrome c reductase complex (complex III or cytochrome b-c1 complex), which is a respiratory chain that generates an electrochemical potential coupled to ATP synthesis. ATP synthase F0 subunit 6 (or subunit/chain A) is a subunit of F0 complex of transmembrane F-type ATP synthase. This subunit is a key component of the proton channel, and may play a direct role in the translocation of protons across the membrane. ATP6 is a gene associated with neuropathy, ataxia, and retinitis pigmentosa. mt-ATP8 is another subunit involved in ATP biosynthetic process.

TABLE 4

| Gene | Locus | Vehicle FPKM | MARCKS FPKM | Ln (Fold Change) (M/V) | P-Value |
|---|---|---|---|---|---|
| Non-Annotated | chrM: 1093-2664 | 53178.50 | 36802.40 | 0.69205412 | <1.00E−12 |
| Mitochondrial NADH dehydrogenase subunit 5 mt-nd5 | chrM: 11735-14061 | 2920.80 | 2501.19 | 0.856337305 | 1.46E−09 |
| Mitochondrial NADH dehydrogenase subunit 6 mt-nd6 | chrM: 11735-14061 | 1073.10 | 530.91 | 0.49473954 | <1.00E−12 |
| Cytochrome b (mt-cyb) | chrM: 14135-15278 | 2792.49 | 2104.37 | 0.753581929 | <1.00E−12 |
| Non-Annotated | chrM: 2739-3831 | 51.90 | 0.00 | 0 | <1.00E−12 |
| Non-Annotated | chrM: 2739-3831 | 126.72 | 0.00 | 0 | <1.00E−12 |
| Mitochondrial NADH dehydrogenase subunit 1 mt-nd1 | chrM: 2739-3831 | 1879.89 | 1473.47 | 0.783806499 | 2.51E−12 |
| Mitochondrial NADH dehydrogenase subunit 2 mt-nd2 | chrM: 3903-5008 | 1965.45 | 1122.94 | 0.571339897 | <1.00E−12 |
| Non-Annotated | chrM: 5322-6933 | 321.91 | 0.00 | 0 | <1.00E−12 |
| Cytochrome c oxidase subunit I mt-co1 | chrM: 5322-6933 | 9734.89 | 7200.89 | 0.739699165 | <1.00E−12 |
| Non-Annotated | chrM: 67-1025 | 69491.10 | 57596.80 | 0.828837074 | <1.00E−12 |
| Cytochrome c oxidase subunit 2 mt-co2 | chrM: 7005-7689 | 5773.44 | 3759.79 | 0.651221802 | <1.00E−12 |
| ATP synthase F0 subunit 6 mt-ATP6 | chrM: 7757-9382 | 3257.55 | 1801.13 | 0.552909395 | <1.00E−12 |
| ATP synthase F0 subunit 8 mt-ATP8 | chrM: 7757-9382 | 3627.88 | 2589.08 | 0.713661973 | <1.00E−12 |
| Cytochrome c oxidase subunit 3 mt-co3 | chrM: 7757-9382 | 5137.18 | 2736.25 | 0.532636583 | <1.00E−12 |
| Mitochondrial NADH dehydrogenase subunit 3 mt-nd3 | chrM: 9450-9798 | 617.42 | 324.46 | 0.525503833 | <1.00E−12 |
| NADH dehydrogenase subunit 4L mt-ND4L | chrM: 9869-11537 | 5804.14 | 4168.41 | 0.718178748 | <1.00E−12 |
| Mitochondrial NADH dehydrogenase subunit 4 mt-nd4 | chrM: 9869-11537 | 2440.82 | 1684.95 | 0.690321285 | <1.00E−12 |

Table 5 provides the list of the genes that are directly or indirectly associated with neurological function and are with significant fold change in peptide decoy treated animals in comparison to the controls.

TABLE 5

| Gene | Locus | Vehicle FPKM | MARCKS FPKM | Ln (Fold Change) (M/V) | P-Value |
|---|---|---|---|---|---|
| Ywhae | chr10: 63072127-63109833 | 892.66 | 584.35 | 0.654609858 | 1.78E-15 |
| HPCA_RAT | chr5: 148268061-148276223 | 141.44 | 315.32 | 2.229369344 | 2.44E-15 |
| Sdcbp | chr5: 19822457-19849209 | 131.61 | 87.65 | 0.665954715 | 0.003191 |
| Snap25 | chr3: 124860288-124894636 | 750.47 | 613.59 | 0.817613323 | 0.0002361 |
| Ndrg2 | chr15: 27338551-27347196 | 142.86 | 60.35 | 0.422424365 | 0.0010441 |
| Rraga | chr5: 105659673-105661250 | 433.02 | 207.77 | 0.479822088 | 0 |
| Ywhab | chr3: 154926026-155140469 | 131.57 | 67.59 | 0.513743017 | 2.47E-07 |
| NU3M_RAT | chrM: 9450-9798 | 617.42 | 324.46 | 0.525503833 | 0 |
| Aldoc | chr10: 64308825-64312415 | 140.11 | 74.57 | 0.53221158 | 0.000264 |
| Selt | chr2: 147913244-147929296 | 214.44 | 115.30 | 0.537667352 | 7.73E-08 |
| Tuba1b | chr7: 137706855-137709839 | 219.23 | 118.09 | 0.538661193 | 5.96E-08 |
| Gpm6a | chr16: 39670749-39783384 | 311.49 | 177.84 | 0.570909873 | 2.46E-09 |
| Gdi1 | chrX: 160299116-160305777 | 124.22 | 82.82 | 0.666709064 | 0.004267 |
| P97600_RAT | chr1: 249369571-249369889 | 492.68 | 371.65 | 0.754352742 | 4.08E-05 |
| Calm-ps2 | chr15: 64161641-64162753 | 383.97 | 299.19 | 0.779195716 | 0.0012151 |
| Mt3 | chr19: 11284554-11286402 | 301.07 | 396.12 | 1.315715002 | 0.0003324 |
| Fth1 | chr1: 212430422-212432741 | 354.58 | 495.44 | 1.397279011 | 1.52E-06 |
| Slc25a4 | chr16: 49353475-49357271 | 243.91 | 383.20 | 1.571039674 | 3.49E-08 |
| RTN1_RAT | chr6: 94397064-94426283 | 842.08 | 1453.43 | 1.726006054 | 0 |
| Calm3 | chr1: 77244168-77252808 | 856.54 | 1621.94 | 1.89359074 | 0 |

Among the genes identified in Table 5, Ywhae (tyrosine 3-monooxygenase/tryptophan 5-monooxygenase activation protein, epsilon Polypeptide; UniProtKB: P62258) belongs to the 14-3-3 family of proteins which mediate signal transduction by binding to phosphoserine-containing proteins.

HPCA is a neuron-specific calcium-binding protein hippocalcin (UniProtKB:P84076). HPCA is an actin binding protein, and it may be involved in the calcium-dependent regulation of rhodopsin phosphorylation.

Sdcbp (syndecan binding protein or syntenin; UniProtKB: O00560), is a protein initially identified as a molecule linking syndecan-mediated signaling to the cytoskeleton. It may function as an adapter protein.

Snap25 (Synaptosomal-associated protein 25; UniProtKB: P60880) encodes SNAP-25 protein, a component of the SNARE complex, which is proposed to account for the specificity of membrane fusion and to directly execute fusion by forming a tight complex that brings the synaptic vesicle and plasma membranes together. t-SNARE involved in the molecular regulation of neurotransmitter release. SNAP-25 May play an important role in the synaptic function of specific neuronal systems, it may associate with proteins involved in vesicle docking and membrane fusion, and it regulates plasma membrane recycling as well.

Ndrg2 (N-myc downstream regulator 2; UniProtKB: Q9UN36) is a member of the N-myc downregulated gene family which belongs to the alpha/beta hydrolase superfamily. The protein encoded by this gene is a cytoplasmic protein that may play a role in neurite outgrowth. This gene may be involved in glioblastoma carcinogenesis. The Ndrg2 protein may be involved in dendritic cell and neuron differentiation, and it may have anti-tumor activity.

Rraga (Ras-related GTP binding A; UniProtKB: Q7L523) encodes a protein that may play a direct role in a TNF-alpha signaling pathway leading to induction of cell death.

Ywhab (tyrosine 3-monooxygenase/tryptophan 5-monooxygenase activation protein, beta Polypeptide; UniProtKB: P31946) encodes a protein belonging to the 14-3-3 family of proteins, members of which mediate signal transduction by binding to phosphoserine-containing proteins. This protein may play a role in linking mitogenic signaling and the cell cycle machinery.

NU3M (NADH dehydrogenase, subunit 3; UniProtKB: P03897) encodes a protein that is a core subunit of the mitochondrial membrane respiratory chain NADH dehydrogenase (Complex I), functioning in the transfer of electrons from NADH to the respiratory chain.

Aldoc (aldolase C, fructose-bisphosphate; UniProtKB: P09972) is a member of the class I fructose-biphosphate aldolase gene family. This gene expresses specifically in the hippocampus and Purkinje cells of the brain. The encoded protein is a glycolytic enzyme that catalyzes the reversible aldol cleavage of fructose-1,6-biphosphate and fructose 1-phosphate to dihydroxyacetone phosphate and either glyceraldehyde-3-phosphate or glyceraldehyde, respectively.

Selt (selenoprotein T; UniProtKB: P62341) is a gene encoding a selenoprotein, which contains a selenocysteine (Sec) residue at its active site. The selenocysteine is encoded by the UGA codon that normally signals translation termination. The 3' UTR of selenoprotein genes have a common stem-loop structure, the sec insertion sequence (SECIS), that is necessary for the recognition of UGA as a Sec codon rather than as a stop signal.

Tuba1b (tubulin, alpha 1b; UniProtKB: P68363) encodes a subunit of Tubulin, which is the major constituent of microtubules. Tubulin binds two moles of GTP, one at an exchangeable site on the beta chain and one at a non-exchangeable site on the alpha-chain. Microtubules act as a scaffold to determine cell shape, and provide a backbone for cell organelles and vesicles to move on, a process that requires motor proteins.

Gpm6a (glycoprotein M6A; UniProtKB: P51674) encodes Glycoprotein M6A (GPM6A), known as a transmembrane protein. GPM6A is an abundant cell surface protein on neurons in the central nervous system (CNS). The expression level of GPM6A is associated with the differentiation of neurons.

Gdi1 (GDP dissociation inhibitor 1; UniProtKB: P31150) encodes a GDP dissociation inhibitor protein that regulate the GDP-GTP exchange reaction of members of the rab family, small GTP-binding proteins of the ras superfamily. GDIs are involved in vesicular trafficking of molecules between cellular organelles. GDIs slow the rate of dissociation of GDP from rab proteins and release GDP from membrane-bound rabs. GDI1 is expressed primarily in neural and sensory tissues. Mutations in GDI1 have been linked to X-linked non-specific mental retardation.

Scd (Stearyl-CoA desaturase 2; UniProtKB: P97600) encodes an enzyme involved in the regulation of oleic acid synthesis in the peripheral nervous system.

Calm-ps2 is a pseudogene of calmodulin 1 (phosphorylase kinase, delta), which encodes a member of the EF-hand calcium-binding protein family.

Mt3 (metallothionein 3; UniProtKB: P25713) encodes a protein that binds heavy metals. Metallothionein contains three zinc and three copper atoms per polypeptide chain and only a negligible amount of cadmium. Metallothionein inhibits survival and neurite formation of cortical neurons in vitro.

Fth1 (ferritin, heavy polypeptide 1; UniProtKB: P02794) encodes the heavy subunit of ferritin, the major intracellular iron storage protein in prokaryotes and eukaryotes. Ferritin is composed of 24 subunits of the heavy and light ferritin chains. Variation in ferritin subunit composition may affect the rates of iron uptake and release in different tissues. A major function of ferritin is the storage of iron in a soluble and nontoxic state. Defects in ferritin proteins are associated with several neurodegenerative diseases.

Slc25a4 (solute carrier family 25 (mitochondrial carrier; adenine nucleotide translocator), member 4; UniProtKB: P12235) gene is a member of the mitochondrial carrier subfamily of solute carrier protein genes. The product of this gene functions as a gated pore that translocates ADP from the mitochondrial matrix into the cytoplasm. The protein forms a homodimer embedded in the inner mitochondria membrane. Mutations in this gene have been shown to result in autosomal dominant progressive external opthalmoplegia and familial hypertrophic cardiomyopathy.

RTN1 (Neuroendocrine-specific protein; reticulon 1; UniProtKB: Q16799) belongs to the family of reticulon encoding genes. The encoded protein, reticulon, is associated with the endoplasmic reticulum, and is involved in neuroendocrine secretion or in membrane trafficking in neuroendocrine cells.

Calm3 (calmodulin 3 (phosphorylase kinase, delta); UniProtKB: P62158) encodes Calmodulin, which mediates the control of a large number of enzymes and other proteins by Ca(2+). Among the enzymes to be stimulated by the calmodulin-Ca(2+) complex are a number of protein kinases and phosphatases. Together with CEP110 and centrin, Calmodulin is involved in a genetic pathway that regulates the centrosome cycle and progression through cytokinesis.

What is claimed is:

1. A biologically active fusion peptide comprising:
   an isolated first peptide having an amino acid sequence of SEQ ID NO: 2; and
   an isolated second peptide consisting of amino acids 156-174 of SEQ ID NO: 3, wherein the second peptide is operably linked to the first peptide.

2. The peptide of claim 1 wherein the biologically active peptide is capable of translocating across a biological membrane.

3. The peptide of claim 1 further comprising a label.

4. The peptide of claim 3, wherein the label is selected from the group consisting of radioisotopes, radionuclides, fluorescent labels, enzymatic labels, chemiluminescent markers, biotinyl groups, predetermined polypeptide epitopes recognized by a secondary reporter, magnetic agents, toxins, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin.

5. The peptide of claim 3 wherein the label comprises a detectable label.

6. The peptide of claim 1 wherein the peptide comprises an amino acid sequence of SEQ ID NO: 1.

7. A method of enhancing memory in a subject comprising administering a first treatment modality comprising an effective amount of a first pharmaceutical composition comprising a peptide comprising an amino acid sequence of SEQ ID NO: 1 to the subject.

8. The method of claim 7 wherein the first pharmaceutical composition further comprises a pharmaceutically acceptable carrier.

9. The method of claim 7 wherein the subject is a mammal.

10. The method of claim 7 wherein the subject presents with memory loss.

11. The method of claim 7 further comprising the step of administering a second treatment modality to the subject.

12. The method of claim 11 wherein the second treatment modality comprises a second pharmaceutical composition.

13. The method of claim 12 wherein administering the second pharmaceutical composition is concurrent with administering the first pharmaceutical composition.

14. The method of claim 12 wherein the second pharmaceutical composition comprises a pharmaceutically acceptable carrier.

15. The method of claim 12 wherein administering the second pharmaceutical composition is subsequent to administering the first pharmaceutical composition.

* * * * *

```
                        SEQUENCE LISTING

<160> NUMBER OF SEQ ID NOS: 3

<210> SEQ ID NO 1
<211> LENGTH: 30
<212> TYPE: PRT
<213> ORGANISM: Artificial Sequence
<220> FEATURE:
<223> OTHER INFORMATION: TAT MARCKS fusion

<400> SEQUENCE: 1

Tyr Gly Arg Lys Lys Arg Arg Gln Arg Arg Cys Lys Arg Phe Ser
1               5                   10                  15

Phe Lys Lys Ser Phe Lys Leu Ser Gly Phe Ser Phe Lys Lys
            20                  25                  30

<210> SEQ ID NO 2
<211> LENGTH: 12
<212> TYPE: PRT
<213> ORGANISM: Human immunodeficiency virus type 1
<220> FEATURE:
<221> NAME/KEY: MISC_FEATURE
<223> OTHER INFORMATION: TAT transduction domain

<400> SEQUENCE: 2

Tyr Gly Arg Lys Lys Arg Arg Gln Arg Arg Arg Cys
1               5                   10

<210> SEQ ID NO 3
<211> LENGTH: 332
<212> TYPE: PRT
<213> ORGANISM: Homo sapiens
<220> FEATURE:
<221> NAME/KEY: MISC_FEATURE
<223> OTHER INFORMATION: Full length human MARCKS protein

<400> SEQUENCE: 3

Met Gly Ala Gln Phe Ser Lys Thr Ala Ala Lys Gly Glu Ala Ala Ala
1               5                   10                  15
```

-continued

```
Glu Arg Pro Gly Glu Ala Ala Val Ala Ser Ser Pro Ser Lys Ala Asn
            20              25              30

Gly Gln Glu Asn Gly His Val Lys Val Asn Gly Asp Ala Ser Pro Ala
        35              40              45

Ala Ala Glu Ser Gly Ala Lys Glu Glu Leu Gln Ala Asn Gly Ser Ala
    50              55              60

Pro Ala Ala Asp Lys Glu Glu Pro Ala Ala Gly Ser Gly Ala Ala
65              70              75              80

Ser Pro Ser Ala Ala Glu Lys Gly Glu Pro Ala Ala Ala Ala Pro
            85              90              95

Glu Ala Gly Ala Ser Pro Val Glu Lys Glu Ala Pro Ala Glu Gly Glu
            100             105             110

Ala Ala Glu Pro Gly Ser Pro Thr Ala Ala Glu Gly Glu Ala Ala Ser
            115             120             125

Ala Ala Ser Ser Thr Ser Ser Pro Lys Ala Glu Asp Gly Ala Thr Pro
            130             135             140

Ser Pro Ser Asn Glu Thr Pro Lys Lys Lys Lys Arg Phe Ser Phe
145             150             155             160

Lys Lys Ser Phe Lys Leu Ser Gly Phe Ser Phe Lys Lys Asn Lys Lys
                165             170             175

Glu Ala Gly Glu Gly Gly Glu Ala Glu Ala Pro Ala Ala Glu Gly Gly
            180             185             190

Lys Asp Glu Ala Ala Gly Gly Ala Ala Ala Ala Ala Glu Ala Gly
        195             200             205

Ala Ala Ser Gly Glu Gln Ala Ala Ala Pro Gly Glu Glu Ala Ala Ala
    210             215             220

Gly Glu Glu Gly Ala Ala Gly Gly Asp Pro Gln Glu Ala Lys Pro Gln
225             230             235             240

Glu Ala Ala Val Ala Pro Glu Lys Pro Pro Ala Ser Asp Glu Thr Lys
            245             250             255

Ala Ala Glu Glu Pro Ser Lys Val Glu Glu Lys Lys Ala Glu Glu Ala
            260             265             270

Gly Ala Ser Ala Ala Ala Cys Glu Ala Pro Ser Ala Ala Gly Pro Gly
        275             280             285

Ala Pro Pro Glu Gln Glu Ala Ala Pro Ala Glu Glu Pro Ala Ala Ala
    290             295             300

Ala Ala Ser Ser Ala Cys Ala Ala Pro Ser Gln Glu Ala Gln Pro Glu
305             310             315             320

Cys Ser Pro Glu Ala Pro Pro Ala Glu Ala Ala Glu
            325             330
```